United States Patent [19]

Menart et al.

[11] Patent Number: 5,631,143
[45] Date of Patent: May 20, 1997

[54] *K. LACTIS* PYRUVATE-DECARBOXYLASE PROMOTER AND USE THEREOF

[75] Inventors: Sandrine Menart, Les Ulis; Monique Bolotin, Gif-sur-Yvette, both of France

[73] Assignee: Rhone-Poulenc Rorer S.A., Antony, France

[21] Appl. No.: 362,511

[22] PCT Filed: Jul. 6, 1993

[86] PCT No.: PCT/FR93/00694

§ 371 Date: Feb. 1, 1995

§ 102(e) Date: Feb. 1, 1995

[87] PCT Pub. No.: WO94/01569

PCT Pub. Date: Jan. 20, 1994

[30] Foreign Application Priority Data

Jul. 8, 1992 [FR] France ................................ 92 08428

[51] Int. Cl.$^6$ ........................ C12P 21/02; C12N 15/14; C12N 15/81; C07N 21/04
[52] U.S. Cl. ................ 435/69.1; 435/70.1; 536/23.1; 536/23.5; 536/24.1; 935/28; 935/37
[58] Field of Search ..................... 435/69.1, 69.2, 435/69.3, 69.4, 69.5, 69.51, 69.52, 69.6, 69.7, 69.8, 69.9, 70.1, 183; 536/23.1, 23.2, 23.4, 23.5, 24.1; 935/22, 28, 33, 37, 47

[56] References Cited

U.S. PATENT DOCUMENTS

| 4,943,529 | 7/1990 | Van den Berg et al. | 435/172.3 |
| 5,223,408 | 6/1993 | Goeddel et al. | 435/69.3 |

FOREIGN PATENT DOCUMENTS 0361991  4/1990  European Pat. Off. .

OTHER PUBLICATIONS

Chen et al. "A Gene Cloning System for *Kluyveromyces lactis*" J Basic Microbiol. 28(4) 211–220 1988.
Verduyn et al. "Effect of Beuzoic Acid on Metabolic Fluxes In Yeasts . . ."Yeast 8: 501–517 1992.
Kellerman et al. "The Glucose–and ethanol–dependent Regulation of POCI from *Saccharomyces cerevisiae* . . . " CurrGenet. 14: 337–344 1988.
Conway et al. "Promoter & Nucleotide Sequence of the *Tumomonas mobilis* Pyruvate Decarboxylase" 169(3): J Bacteriol 949–954 1987.
Kellerman et al "Andysis of the Primary Structure and Promoter Function of A Pyruvate Decarboxylase Gene . . . " Nucleic Acids Res. 14(22) 8963–8977 1986.

*Primary Examiner*—Mindy Fleisher
*Assistant Examiner*—Nancy T. Degen

[57] ABSTRACT

The present invention concerns DNA sequences comprising all or part of the *K. lactis* promoter gene PDC1 or a derivative thereof, and having transcriptional promoter activity. The invention also relates to the use of the sequences for the expression of recombinant genes.

12 Claims, 4 Drawing Sheets

K. LACTIS PYRUVATE-DECARBOXYLASE PROMOTER AND USE THEREOF

The present invention relates to the field of molecular biology. More particularly, it relates to a novel DNA sequence having a transcriptional promoter activity, expression vectors containing this sequence, and its use for the production of recombinant proteins, and, for example, heterologous proteins. The invention also relates to recombinant cells containing this DNA sequence.

The progress made in the field of molecular biology has enabled microorganisms to be modified to make them produce heterologous proteins. In particular, numerous genetic studies have focused on the bacteria $E.\ coli$. However, the industrial application of these novel methods of production is still limited, in particular by the problems of efficiency of expression of the genes in these recombinant microorganisms. In addition, with the aim of increasing the performance of these production systems, research has been carried out in order to isolate strong promoters enabling high levels of expression of heterologous proteins to be obtained. For $E.\ coli$, the promoters of the tryptophan and lactose operons can be mentioned in particular.

More recently, with the yeast $S.\ cerevisiae$, studies have focused on promoters derived from genes implicated in glycolysis. The studies on the promoter of the gene of 3-phosphoglycerate kinase PGK (Dobson et al., Nucleic Acid Res. 10, 1982, 2625; Hitzeman et al., Nucleic Acid Research 1982, 7791), on that of the gene of glyceraldehyde-3-phosphate dehydrogenase GAPDH (Holland et al., J. Biol. Chem. 254, 1979, 9839; Musti et al., Gene 25, 1983, 133), on that of the gene of alcohol dehydrogenase 1 ADH1 (Bennentzen et al., J. Biol. Chem. 257, 1982, 3018; Denis et al., J. Biol. Chem. 25, 1983, 1165), on that of the gene of enolase 1 ENO1 (Uemura et al., Gene 45, 1986, 65), on that of the gene GAL1/GAL10 (Johnson and Davis, Mol. Cell. Biol. 4 (1984) 1440) or on that of the gene CYC1 (Guarente and Ptashne, PNAS 78 (1981) 2199) may be mentioned especially.

Recently, genetic tools have been developed so as to make use of the yeast Kluyveromyces as host cell for the production of recombinant proteins. The recognition of a two-micron type plasmid native to $K.\ drosophilarum$ (plasmid PKD1—EP 241 435) has allowed a very efficient host/vector system for the production of recombinant proteins to be established (EP 361 991). However, the promoters used in this system have not been optimized until now. In particular, they are essentially heterologous promoters, that is to say originating from other microorganisms, such as especially $S.\ cerevisiae$. This situation can produce various disadvantages, and especially limit the activity of the promoter because of the absence of certain elements of the trans-criptional machinery (for example of trans-activators), exhibit a certain toxicity for the host cell due to an absence of regulation, or affect the stability of the vector.

Under these conditions, the lack of strong homologous promoters in Kluyveromyces constitutes a limiting factor in the industrial exploitation of this expression system.

The Applicant has now identified, cloned and sequenced a region of the genome of $Kluyveromyces\ lactis$ presenting a transcriptional promoter activity (see SEQ ID No. 1 and 2). More precisely, this region corresponds to the promoter of the gene encoding the pyruvate decarboxylase of $K.\ lactis$ (K1PDC1). This region, or derivatives or fragments of the latter, can be utilized in a very effective manner for the production of recombinant proteins in the yeasts of the genus Kluyveromyces. It is understood that this sequence can also be used in other host organisms.

Moreover, an advantage of the promoter region obtained lies in the absence of suppression by glucose, allowing use in conventional and industrial culture media.

One subject of the present invention therefore lies in a DNA sequence comprising all or part of the sequence SEQ ID No. 1 or of its complementary strand, or of a derivative of the latter, and possessing a transcriptional promoter activity.

In the sense of the present invention, derivative is understood as meaning any sequence obtained from the sequence SEQ ID No. 1 by modification(s) of genetic and/or chemical nature, retaining a promoter activity. Modification of genetic and/or chemical nature is understood as meaning any mutation, deletion, substitution, addition and/or modification of one or more nucleotides. Such modifications can be carried out with various aims, and especially that of preparing portable promoters, or that of preparing promoters adapted to expression in a particular type of vector or host, that of reducing the size, of increasing the activity of transcription promoter, of generating inducible promoters, of improving the level of regulation, or even of changing the nature of the regulation. Such modifications can be carried out, for example, by mutagenesis in vitro, by introduction of additional control elements or of synthetic sequences, or by deletions or substitutions of the original control elements.

When a derivative such as defined above is produced, its transcriptional promoter activity can be demonstrated in several ways, and in particular by placing under the control of the sequence studied a reporter gene whose expression is detectable. Any other technique known to the person skilled in the art can quite obviously be used to this effect.

The sequence SEQ ID No. 1 was obtained from a fusion bank between fragments of the genome of $K.\ lactis$ 2359/152 and the lacZ gene of $E.\ coli$ according to the protocol described in the examples. It is understood that the specialist can isolate this region by hybridization by means of a probe comprising all or part of the sequence SEQ ID No. 1 or of its complementary strand. The derivatives according to the invention can then be prepared from this sequence, as indicated in the examples.

Another object of the invention relates to a recombinant DNA comprising a sequence of DNA such as defined above.

This recombinant DNA can contain, for example, the promoter sequence SEQ ID No. 1 or a derivative of the latter in which is inserted a restriction site facilitating the use of this sequence as a "portable" promoter (SEQ ID No. 4).

Preferentially, this recombinant DNA in addition contains one or more structural genes. In particular, these can be genes coding for proteins of pharmaceutical or food-processing interest. By way of example, enzymes (such as, especially, superoxide dismutase, catalase, amylases, lipases, amidases, chymosin, etc.), blood derivatives (such as serum albumin, alpha- or beta-globin, factor VIII, factor IX, von Willsbrand factor, fibronectin, alpha-1 antitrypsin, etc.), insulin and its variants, lymphokines (such as interleukins, interferons, colony stimulating factors, tumor necrosis is factor (TNF) TGF-B binding vecector fragment granulocyte colony stimulating factor (G-CSF), granulocyte macrophage colony stimulating factor (GM-CSF), and macrophage colony stimulating factor (M-CSF), etc.), growth factors (such as growth hormone, erythropoietin, fibroblast growth factor (FGF), epidermal growth factor (EFG), platelet derived growth factor (PDGF), transforming growth factor (TGF), etc.), apolipoproteins, antigenic polypeptides for the production of vaccines (hepatitis, cytomegalovirus, Epstein-Barr, herpes, etc.), or even fusions of polypeptides such as, especially, fusions comprising an active part fused to a stabilizer part (for example fusions between albumin or fragments of albumin and the receptor or a part of a virus receptor [CD4, etc.]).

Even more preferentially, the recombinant DNA also contains signals allowing the secretion of the expression product of the said structural gene(s). These signals may correspond to natural secretion signals of the protein in question, but they may be of a different origin. In particular, secretion signals derived from yeast genes can be used, such as those of the genes of the killer toxin (Stark and Boyd, EMBO J. 5 (1986) 1995) or of alpha pheromone (Kurjan and Herskowitz, Cell 30 (1982) 933; Brake et al., Yeast 4 (1988) S436).

In a particular embodiment of the invention, the recombinant DNA is part of an expression plasmid which can be of autonomous or integrative replication.

In particular, autonomous replication vectors can be obtained by using autonomous replication sequences in the chosen host. Especially, in yeast, they can be replication origins derived from plasmids (pKD1, 2μ, etc.), or even chromosomal sequences (ARS).

The integrative vectors can be obtained especially by using homologous sequences in certain regions of the host genome allowing, by homologous recombination, integration of the vector.

Another subject of the invention relates to recombinant cells containing a DNA sequence such as defined above.

Advantageously, the cells are chosen from amongst yeasts, and even more preferentially, amongst yeasts of the genus Kluyveromyces. It is understood, however, that the invention covers all the recombinant cells in which the promoter regions of the invention are active, whether they are eukaryotic or prokaryotic cells. Thus, among eukaryotic cells, vegetable or animal cells, yeasts or fungi can be mentioned. In particular, concerning yeasts, yeasts of the genus Saccharomyces, Pichia, Schwanniomyces or Hansenula can be mentioned. Concerning animal cells, the cells COS, CHO, C127, etc. can be mentioned. Among fungi able to be used in the present invention, *Aspergillus ssp*, or *Trichoderma ssp*, can be mentioned more particularly. As prokaryotic hosts, bacteria such as *Escherichia coli* can be used, or those belonging to the genera Corynebacterium, Bacillus or Streptoymces.

The transcription promoter activity of the sequences of the invention in these different hosts can be confirmed, for example, by introducing into the host cell in question a recombinant DNA comprising, under the control of the promoter sequence studied, a reporter gene whose expression can be demonstrated in the host in question.

The recombinant cells of the invention can be obtained by any method allowing a foreign DNA to he introduced into a cell. It can be especially transformation, electropotation, conjugation, fusion of protoplasts or any other technique known to the person skilled in the art. Concerning transformation, various protocols have been described in the prior art. In particular, it can be carried out by treating the whole cells in the presence of lithium acetate and of polyethylene glycol according to the technique described by Ito et al. (J. Bacteriol. 153 (1983) 163-168), or in the presence of ethylene glycol and dimethyl sulphoxide according to the technique of Durrens et al. (Curr. Genet. 18 (1990) 7). An alternative protocol has also been described in the Patent Application EP 361 991. Concerning electropotation, it can be carried out according to Becker and Guarentte (in: Methods in Enzymology Vol 194 (1991) 182).

Another subject of the invention relates to the use of a sequence such as defined above for the expression of recombinant genes. The DNA sequences according to the invention can in fact allow production of recombinant proteins at high levels.

Advantageously, the sequences of the invention can be used for the expression of genes encoding proteins of pharmaceutical or food-processing interest. By way of example, the proteins listed above may be mentioned.

The present invention also allows a production process for recombinant proteins to be realized, according to which a recombinant cell such as defined above is cultured and the protein produced is recovered. By way of example of protein, the proteins listed above may he mentioned.

Preferentially, the process of the invention is applicable to the production of human serum albumin, or one of its molecular variants. Molecular variant of albumin is understood as meaning the natural variants resulting from the polymorphism of the albumin, the truncated forms, or any hybrid protein based on albumin.

Other advantages of the present invention will become apparent from reading the examples which follow, which may be considered as illustrative and non-limiting.

GENERAL CLONING TECHNIQUES

The methods conventionally used in molecular biology such as preparative extractions of plasmid DNA, centrifugation of plasmid DNA in a caesium chloride gradient, electrophoresis on agarose or acrylamide gels, purification of DNA fragments by electroelution, extraction of proteins with phenol or with phenol/chloroform, precipitation of DNA in saline medium with ethanol or isopropanol, transformation in *Escherichia coli* etc. are well known to the specialist and are profusely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were supplied by New England Biolabs (Biolabs), or Pharmacia and are used according to the recommendations of the suppliers.

The plasmids of type pBR322 and pUC are of commercial origin (Bethesda Research Laboratories).

For the ligations, the DNA fragments are separated according to their size by electrophoresis in agarose or acrylamide gels, extracted with phenol or with a phenol/chloroform mixture, precipitated with ethanol and then incubated in the presence of the DNA ligase of the phage T4 (Boshringer) according to the recommendations of the supplier.

The filling of the prominent 5' ends is carried out by the Klenow fragment of the DNA polymerase I of *E. coli* (Boshringer) according to the specifications of the supplier. The destruction of the prominent 3' ends is carried out in the presence of the DNA polymerase of the phage T4 (Biolabs) used according to the recommendations of the manufacturer. The destruction of the prominent 5' ends is carried out by a treatment managed by the nuclease S1.

The directed mutagenesis in vitro by synthetic oligodeoxynucleotides is carried out according to the method developed by Taylor et al. [Nucleic Acids Res. 13 (1985) 8749–8764].

The enzymatic amplification of DNA fragments by the said technique of PCR [Polymerase-catalysed Chain Reaction, Saiki R. K. et al., Science 230 (1985) 1350–1354; Mullis K. B. and Faloona F. A., Meth. Enzym. 155 (1987) 335–350] is carried out using a "DNA thermal cycler" (Perkin Elmer Cetus) according to the specifications of the manufacturer.

The confirmation of the nucleotide sequences is carried out by the method developed by Sanger et al. [Proc. Natl. Acad. Sci. USA, 74 (1977) 5463–5467].

The transformations of *K. lactis* are carried out by any technique known to the person skilled in the art, and of which an example is given in the text.

Unless stated otherwise, the bacterial strains used are *E. coli* DH1 (Hanahan D., J. Mol. Biol. 166 (1983) 557) or *E. coli* JM109::(Mucts) (Daignan-fornier and Bolotin-Fukuhara, Gene 62 (1988) 45).

The strains of yeasts used belong to budding yeasts and more particularly to yeasts of the genus Kluyveromyces. The strain *K. lactis* 2359/152 and *K. lactis* SD6 were particularly used.

The strains of yeasts transformed by the plasmids are cultured in erlenmeyers or in 2 l pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLES

I—Isolation of the K1PDC1 promoter of *K. lactis*.

The sequence SEQ ID No. 1 was isolated from a fusion bank between fragments of the genome of *K. lactis* 2359/152 and the lacZ gene of *E. coli*. This example describes in (A) the preparation of the fusion bank, and in (B) the selection and the characterization of a clone of this bank bearing the gene promoter of the pyruvate decarboxylase of *K. lactis*.

A/Preparation of the Fusion Bank

Figure 1A:
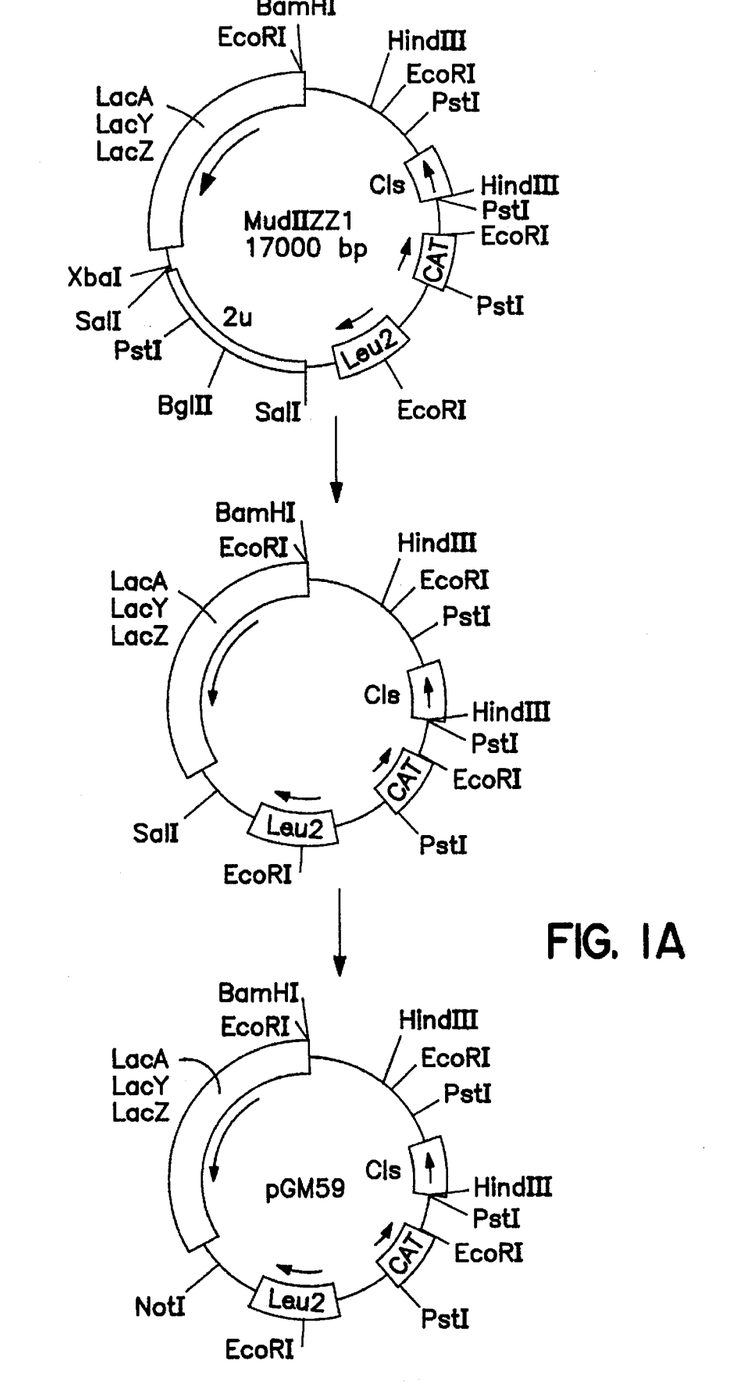
FIGS. 1A & 1B Preparation of the Mini Mu transposon MudIIZK1.
Figure 1B:
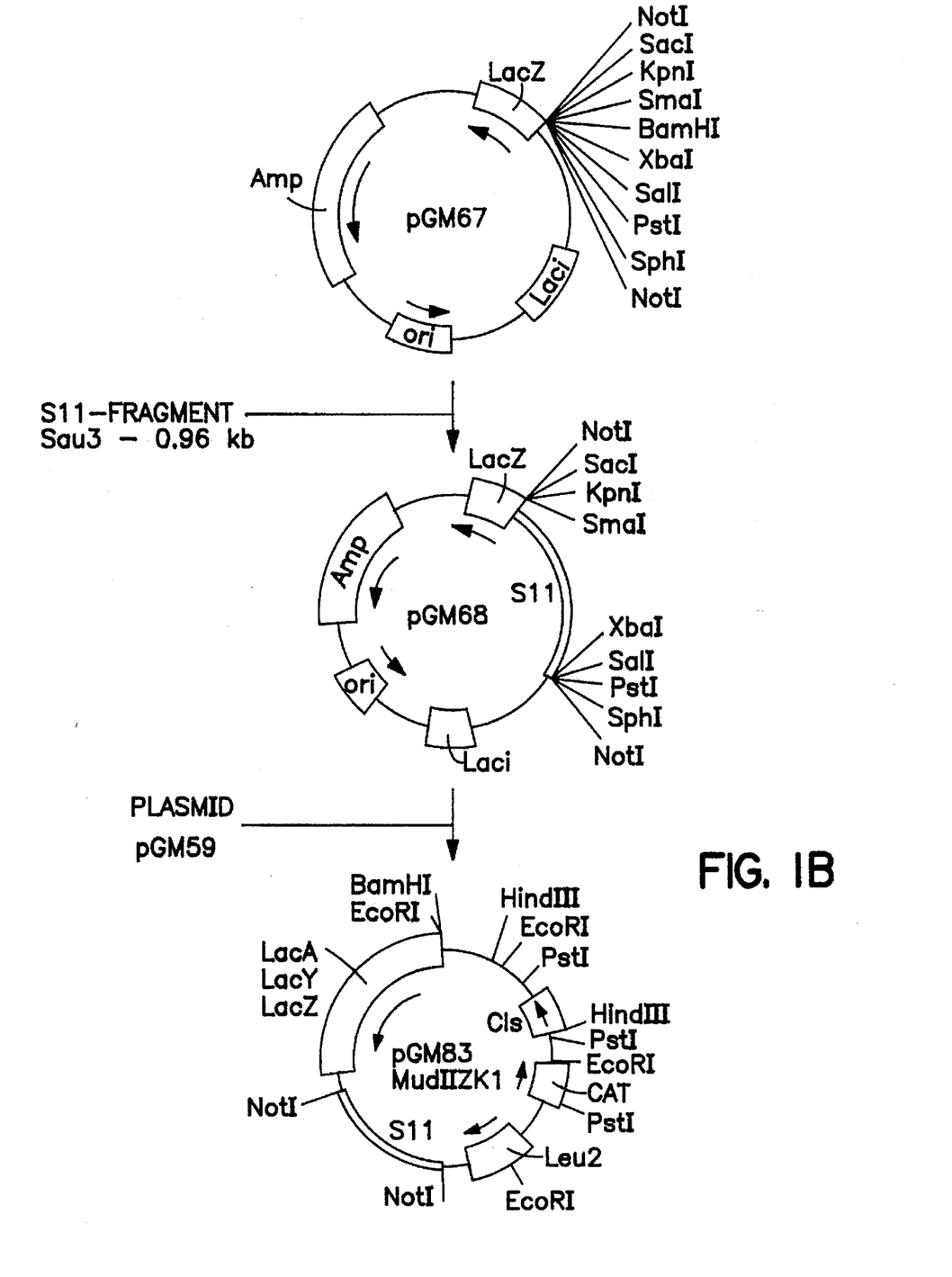
Figure 2:
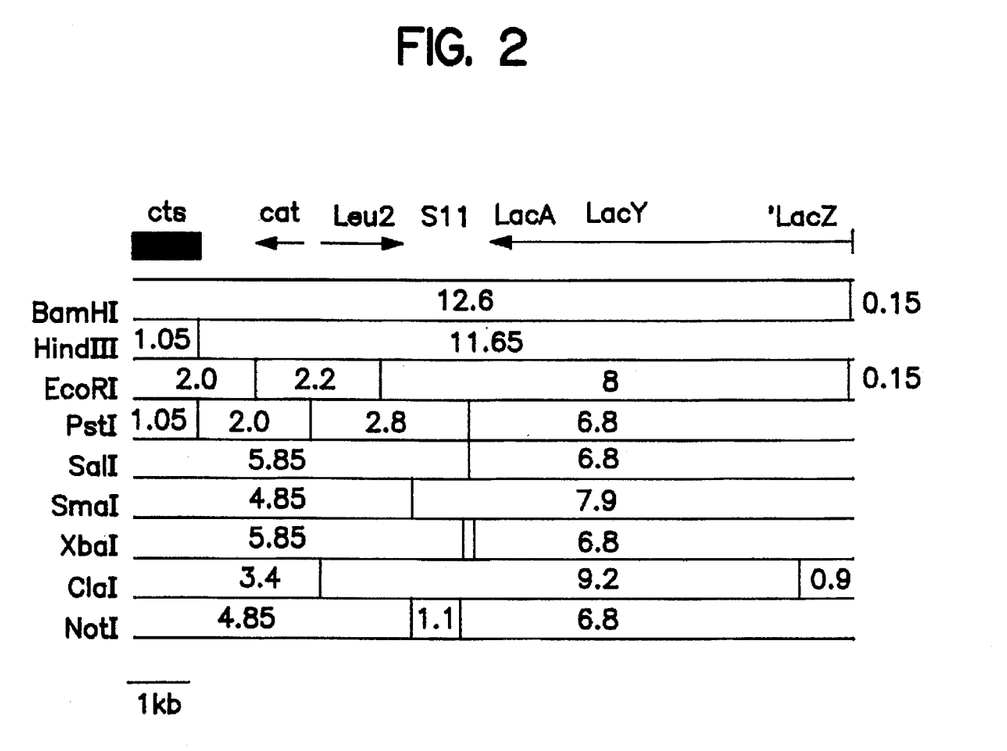
FIG. 2 Restriction map of the Mini Mu transposon MudI-IZK1.

A.1. Preparation of the Mini Mu transposon MudIIZK1 (FIGS. 1 and 2).

The Mini Mu MudIIZK1 was constructed from Mini Mu MudIIZZ1 described by Daignan-Fornier and Bolotin-Fukuhara (Gene 62 (1988) 45). It was obtained by substituting the replication origin of the mini transposon MudIIZZ1 by a functional replication origin in Kluyveromyces: the origin of replication of the plasmid pKD1 (EP231 435).

A.1.1. Construction of a cassette bearing the replication origin of the plasmid pKD1 (fragment s11).

In order to facilitate the subsequent operations, the fragment S11 (bearing the replication origin of the plasmid pKD1) was put in the form of a cassette NotI. For this, a derivative of the plasmid pUC18 was constructed in which the external sites of the cloning multisite (HindIII and EcoRI sites) were changed to NotI sites. This was done by digestion with the corresponding enzyme, action of the Klenow enzyme and ligation with a synthetic oligonucleotide corresponding to an NotI site [oligo d(AGCGGCCGCT) (SEQ ID No. 5); Biolabs]. The plasmid obtained is designated pGM67. The 960 bp fragment S11 obtained by digestion with the enzyme Sau3A of the plasmid KEp6 (Chen et al., Nucl. Acids Res. 114 (1986) 4471) was then inserted in the BamHI compatible site of the plasmid pGM67. The plasmid thus obtained designated pGM68 contains, in the form of a NotI cassette, the fragment S11.

A.1.2. Suppression of the 2μReplication origin of the MudIIZZ1 transposon.

The plasmid pGM15 bearing the mini Mu MudIIZZ1 (Daignan-Fornier and Bolotin-Fukuhara loc. cit.) was deleted from the 2μregions by digestion by means of the enzyme SalI. The unique SalI site thus obtained was then transformed to a NotI site by ligation of a synthetic oligonucleotide corresponding to an NotI site after action of the Klenow enzyme. The resulting plasmid is called pGM59.

A.1.3. Insertion of the Fragment S11

The cassette NotI bearing the replication origin of the plasmid pKD1 (fragment S11) coming from the modified plasmid pUC18 was then introduced in the unique NotI site of the plasmid pGM59.

The plasmid obtained, designated pGM83, bears a mini Mu, called MudIIZK1, which is adapted to the yeast *Kluyveromyces lactis*, as well as a functional copy of the gene LEU2 of *S. cerevisiae* capable of complementing a leu2 mutation in *K. lactis* (Kämper et al., Curr. Genet. 19 (1991) 109). The restriction map of the mini-mu MudIIZK1 is represented in FIG. 2.

A.2. Introduction of the Mini Mu MudIIZK1 into the strain *E. coli* bearing the Mu helper JM109::(Mucts): obtainment of the strain JM109::(Mucts)::(MudIIZK1).

The strain JM109::(Mucts) was transformed by the plasmid pGM83 containing the mini mu MudIIZK1 in the presence of calcium chloride. After transformation, transposition was then induced by thermal shock according to the technique described by Castilho et al. (J. Bacteriol. 158 (1984) 488). The phage lyeate obtained after induction is then used to superinfect the strain JM109::(Mucts). The strain JM109::(Mucts) being recA, the linear DNA encapsidated by the phage cannot reclose to give a replicative plasmid. The integrants [strain JM109::(Mucts):: (MudIIZK1)] are then selected as chloramphenicol-resistant ($Cm^R$), ampicillin-Sensitive ($Amp^s$) clones.

A.3 Preparation of the Genome Bank of *K. lactis* in *E. coli* DH1

The high-molecular weight DNA was prepared from the strain *K. lactis* 2359/152, and digested partially by the enzyme Sau3A. The fragments of a size of 4 to 8 kb were recovered on LMP ("Low Melting Point", SEAKEM) agarose gel and cloned in the plasmid pBR322 linearized by BamHI and dephosphorylated by action of calf intestinal phosphatase (Biolabs). 35 pools of 1000 colonies in *E. coli* DH1 were thus produced. The 1000 colonies of each pool are ampicillin-resistant and tetracycline-sensitive, which shows that they have all inserted a genomic DNA fragment of *K. lactis* in pBR322.

A.4. Preparation of the Fusion Bank

A.4.1 Introduction of the Genome Bank of *K. lactis* into the strain JM109::(Mucts)::(MudIIZK1).

The plasmid DNA of each pool produced in DH1 is extracted (Maniatis). This DNA is then used to transform the strain JM109::(Mucts)::(MudIIZK1) in the presence of calcium chloride. To be representative of the 1000 colonies contained in each pool of the genome bank, more than 3000 clones per pool were recovered in the strain JM109::(Mucts) ::(MudIIZK1) allowing the transduction.

A.4.2. Transposition of the Mini Mu MudIIZK1

The fusion bank is produced by extensive transposition of the Mini Mu MudIIZK1 in the plasmids forming the genomic DNA bank of *K. lactis*. The mini-muductions were carried out according to the protocol described by Castilho et al. (J. Bacteriol. 158 (1984) 488) and the transductants were selected on LBAC selective medium (LB medium (Gibco BRL) supplemented with 50 mg/l of ampicillin and 30 mg/l of chloramphenicol), the marker $Amp^R$ being contributed by the plasmid and the marker $Cm^R$ by the mini-mu. For each pool, transpositions are done in series, and between 10,000 and 20,000 transductants are recovered per pool. The DNA of the transductants is then extracted from a preparation of 100 ml, purified by precipitation with polyethylene glycol (Maniatis et al., 1989) and resuspended in 100 µl of water. This DNA was then used to transform *K. lactis* and select clones bearing promoters.

B/Isolation of the K1PDC1 Promoter of *K. lactis*

The fusion DNA prepared above was utilized to transform, by electroporation, a receptor strain of *K. lactis*. This receptor strain, designated SD6, bears the mutations leu2 (corresponding to the selection marker of the mini-mu MudIIZK1) and lac4–8. This last mutation prevents the strain from growing on a medium containing lactose as the only source of carbon, but it can be complemented by the superexpression of the lacZ gene of *E. coli* encoding β-galactosidase (Chen et al., J. Basic Microbiol. 28 (1988) 211). Therefore the expression of a protein fused to β-galactosidase may allow the growth of the strain SD6 on lactose after transformation. This positive screen was used to select rapidly clones bearing strong promoters.

B.1. Construction of the Receptor Strain *K. lactis* SD6.

The strain SD6 (Chen et al., Mol. Gen. Genet. 233 (1992) 97) was obtained by growth of the strain *K. lactis* CXJ1-7A (a, lac4–8, ura3A, ade1—1, K1, K2, pKD1) (Chen and Fukuhara, Gene 69 (1988) 181) with the strain AWJ-137 (leu2, trp1, homothallic) (Kämper et al., Curr. Genet. 19 (1991) 109), and selection of the spores having the genotype $ADE^+$, uraA, leu2, lac4–8. As the spores obtained were not capable of regenerating after transformation by protoplasts, a backcrossing was done with the strain CXJ1-7A. After sporulation en masse, the spores of the selected genotype were tested by transformation in lithium chloride with the plasmid KEp6 according to a technique derived from that described by Ito et al. (J. Bacteriol. 153 (1983) 163) (the concentration of LiCl is 20 mM, being 10 times less than that used by Ito for *S. cerevisiae*). The strain CXJ1-7A was used as transformation control.

The strain SD6, selected on these criteria, transforms correctly: 1 to 3×104 transformants per µg of DNA; and the transformants have a satisfactory stability: 30 to 40% of the colonies retain the [$Ura^+$] phenotype after 6 generations in non-selective medium.

B.2. Isolation of the K1PDC1 promoter.

Figure 3:
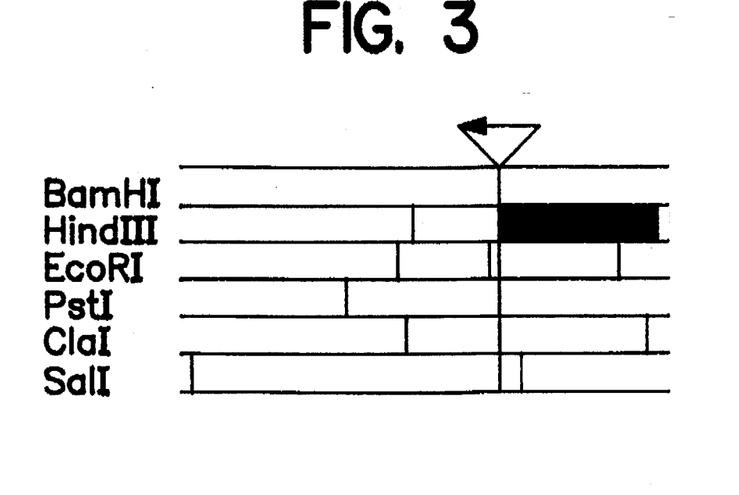
FIG. 3 Restriction map of the clone 1D12.

The strain SD6 was transformed by electropotation according to Becker and Guarante (in Methods in Enzymology vol 194 (1991) 182) (Jouan apparatus; 2500 V/cm; 80–100 ng of DNA/transformation) with the DNA of 11 pools of transductants obtained in A.4.2. (corresponding to a bank of 11,000 clones in *E. coli*). After regenerating for 5 hours in YPD medium (yeast extract 10 g/l; peptone 10 g/l; glucose 20 g/l), the cells were spread on minimum lactose medium. The transformants capable of growing on lactose were restreaked and, tot each clone, the plasmid was extracted, amplified in *E. coli*, and, after rapid verification of the restriction map of the vector and of the mini-mu, used to retransform the yeast SD6. Among the clones of *K. lactis* obtained after retransformation, one of them, the clone 1D12, was studied by restriction (see FIG. 3) and by analysis of the sequence of the Junction between the protein of *K. lactis* and β-galactosidase. For this, the sequence of the junction starting from the lacZ end of the mini-mu (double-stranded sequence) was determined by sequencing by means of the following oligonucleotide situated at −59 nucleotides from the Junction: 5'-CTGTTTCATTTGAAGCGCG-3' (SEQ ID No. 3)

Figure 4:
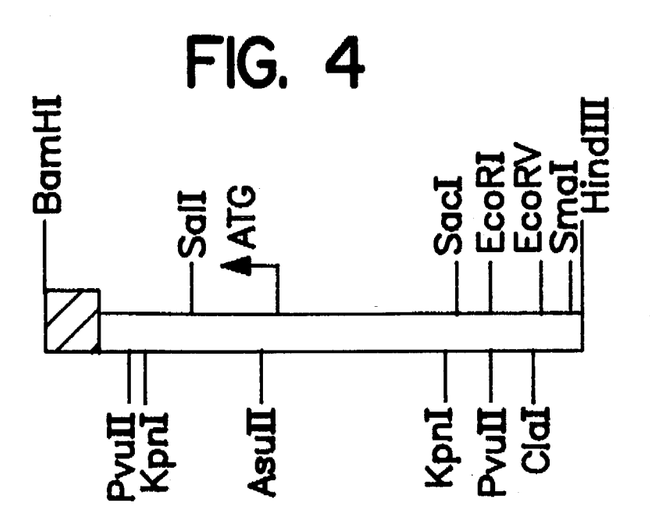
FIG. 4 Restriction map of the 2.05 kb fragment of BamHI-HindIII bearing the promoter K1PDC1.

The analysis of the protein sequence deduced from the nucleotide sequence thus obtained by comparison with the sequences of protein banks of other yeasts or eukaryotes (Ganbank, MIPS, EMBL, etc.), shows that the sequence borne by the clone 1D12 corresponds to the promoter of the pyruvate decarboxylase gene of *K. lactis*. The BamHI-HindIII fragment of 2.05 kb containing the region upstream of the fusion was then subcloned into the vector Bluescript KS+(Stratagene), a restriction map was done (FIG. 4), and the sequence was determined by sequential deletions on 1.2 kb (SEQ ID No. 1). The obtainment of sequence elements also allows the specialist to prepare specific probes and to reclone the promoter region of the invention by hybridization according to the conventional techniques of molecular biology.

II—Transformation of Kluyveromyces

Various techniques permitting the introduction of DNA into the yeast can be used.

Advantageously, the different strains of Kluyveromyces used were transformed by treating the whole cells in the presence of lithium acetate and of polyethylene glycol according to the technique described by Ito et al. (J. Bacteriol. 153 (1983) 163–168). The transformation technique described by Durrens et al. (Curr. Genet. 18 (1990) 7) using ethylene glycol and dimethyl sulphoxide was likewise used. It is also possible to transform yeasts by electroporation, for example according to the method described by Karube et al. (FEBS Letters 182 (1985) 90).

An alternative protocol has already been described in detail in the application EP 361 991.

III—Use of the Promoter SEQ ID No. 1 for Expression of Heterologous Genes.

The transcriptional promoter activity of the region of *K. lactis* described in SEQ ID No. 1 was recognized even at the time of its isolation by its capacity to induce the complementation of the lac4–8 mutation of the strain SD6. This capacity in fact results from the expression of the lacZ gene of *E. coli*, and demonstrates by the same token the capacity of expression of heterologous genes.

IV—Construction of a Portable K1PDC1 Promoter (SEQ ID No. 4)

A portable promoter is prepared by PCR, by insertion in the 2.05 kb BamWI-HindIII fragment of a HindIII restriction site in the +1 position with respect to the codon ATG of the gene K1PCD1 and of the MluI and SalI restriction sites at 1165 bp upstream (SEQ ID No. 4). The PCR product is cloned in the vector pCRII (Invitrogen) to generate the plasmid pYG175, allowing the promoter to be released by simple MluI-HindIII digestion, thus facilitating the cloning in an expression vector.

An expression vector of human serum albumin is then prepared from the plasmid pYG1018 as follows: the plasmid pYG1018 contains the prepro-albumin gene under the control of the LAC4 promoter. It derives from the vector pYG1023 described in the Patent Application EP 402 212 by deletion of the BssHII-MluI fragment bearing the K1PGK gene. 5 µg of the pCRII Promoter and pYG1018 vectors are digested with 60 units of HindIII and of MluI. After migration on agarose gel at 0.8%, the band corresponding to the promoter PDC1 (approximately 1.2 kb), the band corresponding to the vector part (approximately 9 kb) and the band corresponding to the cDNA of the albumin (approximately 2 kb) are electroeluted. Ligation to 3 partners (following the buffer and temperature recommendations defined by the supplier New England Biolabs) is then carried out with 1 μl of promoter DNA, 1 μl of vector DNA and 2 μl of albumin DNA. After transformation in *E. coli* (Chung et al. NAR 16 (1988) 3580), the plasmid DNA of the transformants is prepared according to the technique of alkaline lysis on SDS of Birboim and Doly (NAR 6 (1979) 1513) modified by Ish-Horowicz and Burke (NAR 9 (1981) 2989). After enzymatic digestion, the plasmid possessing the good restriction profile is isolated. This plasmid is designated pYG181.

The strain *K. lactis* CBS 293.91 was transformed by pYG181 under the conditions described in Example II. The production of albumin by several transformants is tested according to the technique described in EP 361 991. The quantity of albumin secreted by the transformants is similar (50–100 mg/l).

---

We claim:

1. A DNA sequence selected from the group consisting of:
   (a) the sequence presented in SEQ ID NO: 1 or SEQ ID NO 4;
   (b) a complementary strand of the sequence presented in SEQ ID NO: 1 or SEQ ID NO 4; and
   (c) a fragment of the sequence of (a) or (b); wherein said DNA sequence possesses transcriptional promoter activity.

2. A recombinant DNA comprising a DNA sequence according to claim 1.

3. A recombinant DNA according to claim 2, further comprising one or more structural genes.

4. A recombinant DNA according to claim 3, further comprising signals enabling secretion of expression products of said one or more structural genes.

5. A recombinant DNA according to claim 3, wherein the one or more structural genes encode proteins of pharmaceutical or food-processing interest.

6. A recombinant DNA according to claim 2, wherein said recombinant DNA is an autonomous or integrative replication vector.

7. A recombinant cell containing a DNA sequence according to claim 1.

8. A recombinant cell according to claim 7, characterized in that said cell is a yeast.

9. A recombinant cell according to claim 8, characterized in that said cell is a yeast of the genus Kluyveromyces.

10. A process for the production of recombinant proteins, comprising culturing a recombinant cell according to claim 7 and recovering the proteins produced.

11. A process according to claim 10, wherein said proteins are of pharmaceutical or food-processing interest.

12. A process according to claim 10, wherein the protein is human serum albumin or a natural variant of human servin albumin resulting from polymorphism.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 1239 base pairs
( B ) TYPE: nucleic acid
( C ) STRANDEDNESS: single
( D ) TOPOLOGY: linear ( i i ) MOLECULE TYPE: cDNA ( i v ) ANTI-SENSE: NO ( v i ) ORIGINAL SOURCE:
( A ) ORGANISM: Kluyveromyces lactis ( i x ) FEATURE:
( A ) NAME/KEY: CDS
( B ) LOCATION: 1177..1239

( x i ) SEQUENCE DESCRIPTION: SEQ ID NO:1:

```
AAGCTTCCAG TCACATGACC TAGAATGCAT ATATTGTCCC GGGTAATATA TAGCAACCGT        60
CTTCTCTCTG CTTATCTCTG GTGCAGCCTC CTAGTTTTTC CGAAAAGTTT CTTTTCTCC       120
AAAATTCTCC GAAAATCGTC AGATATCCAG ATATGCAACA TAGAGGGAAG ATACACCGTT      180
ATATCGATTT CAAAATGCAA ATAACGGCAA CTAAGCCCAT CACTCTCAGC ACGTTTCTTT      240
TCCATGCACG TCGTTCCCAC TGATGATTCC TCGGATCAGT TGATGCGATT TTTAACAACA      300
GCCAAAGCAG ACATCCTCCA AGCCGTATCC CAGACAAATA CAACTCTATC TCTGTGAGGG      360
ATTCGTGTAA ACTGGAATTC AGCTGAGGTA TTTCTTTTTA CAGGATTGCG CTTCCAGTAA      420
ATTCGGTCTG TTCCATTGCG ACTTGTTGAA TGGCATTGGC GATGCCAATC GCAATTCCAT      480
GGGCAACGAG TAAGTAAGTC TCTTCTACAT CGTCCTATTC CTTTCCTAAT GTGAGCTCTT      540
TTTACCTTTT GGTACCCATA CAACGAGTGT CATGGGGAGA GGAAGAGGAA GATTTTAGAT      600
GTAGTGAAAG TGAATAGATG AAATGGGAAA TGGGCGTGTG GTGCGGTTTC TGTGGTATAG      660
AAAATCGGAA ATGAGAGTCA ACCAAGGTAA AAGGTGGGAT AATTTCATGG TATTGGAAAT      720
TATTCAAATT AGCTAACCAT TGCTGGCCCT TGTGCGTGTC CTGTATTTG CATATTCTGT       780
ATTTGCTATG TAGAACCATG GGATAGATTA TGCAATATTT GTGAAAAGAT TCAACCTTTT      840
AAGGTGTATA CGTAGTATTG GCCCATGAAT ATCTTAAGGT TGGAATAGTA GTACCACTTG      900
TGTCAATTAT CCATTAAGGG GGGAGAGTGA GGTGAGAGGC AGGGCTGGCT GGGTGGTGAA      960
TATGACCTTT CTATTTTTTT TAGTTAACTC AGATAAAGTA TAAATACATG GGCATGATTA     1020
TCTGTAATGG CTAGAGTTTC CCATCATGTC TTAATCATAA TCTTAATTAT ATACTTTTGA     1080
TTACCCTCAA AAACCATCCA CTAAAGCCAA ACATATTATA GTATTAACTA TTAATATTAA     1140
GGATAAAACT ACAACTCAAA ACCAACTTAA ATTACA ATG TCT GAA ATT ACA TTA       1194
```

|  |  |  |  |  |  |  |  |  |  | Met | Ser | Glu | Ile | Thr | Leu |  |
|--|--|--|--|--|--|--|--|--|--|--|--|--|--|--|--|--|
|  |  |  |  |  |  |  |  |  |  | 1 |  |  |  | 5 |  |  |

GGT CGT TAC TTG TTC GAA AGA TTA AAG CAA GTC GAA GTT CAA ACC     1239
Gly Arg Tyr Leu Phe Glu Arg Leu Lys Gln Val Glu Val Gln Thr
         10               15               20

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

Met Ser Glu Ile Thr Leu Gly Arg Tyr Leu Phe Glu Arg Leu Lys Gln
 1              5                   10                  15

Val Glu Val Gln Thr
         20

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: other nucleic acid     ( i v ) ANTI-SENSE: NO     ( x i ) SEQUENCE DESCRIPTION: SEQ ID NO:3:

CTGTTTCATT TGAAGCGCG                                                                                   19

( 2 ) INFORMATION FOR SEQ ID NO:4:

( i ) SEQUENCE CHARACTERISTICS:
        ( A ) LENGTH: 1184 base pairs
        ( B ) TYPE: nucleic acid
        ( C ) STRANDEDNESS: single
        ( D ) TOPOLOGY: linear     ( i i ) MOLECULE TYPE: cDNA     ( i v ) ANTI-SENSE: NO     ( v i ) ORIGINAL SOURCE:
        ( A ) ORGANISM: Kluyveromyces lactis     ( x i ) SEQUENCE DESCRIPTION: SEQ ID NO:4:

ACGCGTGTCG ACAGCTTCCA GTCACATGAC CTAGAATGCA TATATTGTCC CGGGTAATAT     60

ATAGCAACCG TCTTCTCTCT GCTTATCTCT GGTGCAGCCT CCTAGTTTTT CCGAAAAGTT     120

TCTTTTTCTC CAAAATTCTC CGAAAATCGT CAGATATCCA GATATGCAAC ATAGAGGGAA     180

GATACACCGT TATATCGATT TCAAAATGCA ATAACGGCA ACTAAGCCCA TCACTCTCAG     240

CACGTTTCTT TTCCATGCAC GTCGTTCCCA CTGATGATTC CTCGGATCAG TTGATGCGAT     300

TTTTAACAAC AGCCAAAGCA GACATCCTCC AAGCCGTATC CCAGACAAAT ACAACTCTAT     360

CTCTGTGAGG GATTCGTGTA AACTGGAATT CAGCTGAGGT ATTTCTTTTT ACAGGATTGC     420

GCTTCCAGTA AATTCGGTCT GTTCCATTGC GACTTGTTGA ATGGCATTGG CGATGCCAAT     480

CGCAATTCCA TGGGCAACGA GTAAGTAAGT CTCTTCTACA TCGTCCTATT CCTTTCCTAA     540

TGTGAGCTCT TTTTACCTTT TGGTACCCAT ACAACGAGTG TCATGGGGAG AGGAAGAGGA     600

```
AGATTTTAGA  TGTAGTGAAA  GTGAATAGAT  GAAATGGGAA  ATGGGCGTGT  GGTGCGGTTT       660

CTGTGGTATA  GAAAATCGGA  AATGAGAGTC  AACCAAGGTA  AAAGGTGGGA  TAATTTCATG       720

GTATTGGAAA  TTATTCAAAT  TAGCTAACCA  TTGCTGGCCC  TTGTGCGTGT  CCTGTATTTT       780

GCATATTCTG  TATTTGCTAT  GTAGAACCAT  GGGATAGATT  ATGCAATATT  TGTGAAAAGA       840

TTCAACCTTT  TAAGGTGTAT  ACGTAGTATT  GGCCCATGAA  TATCTTAAGG  TTGGAATAGT       900

AGTACCACTT  GTGTCAATTA  TCCATTAAGG  GGGGAGAGTG  AGGTGAGAGG  CAGGGCTGGC       960

TGGGTGGTGA  ATATGACCTT  TCTATTTTTT  TTAGTTAACT  CAGATAAAGT  ATAAATACAT      1020

GGGCATGATT  ATCTGTAATG  GCTAGAGTTT  CCCATCATGT  CTTAATCATA  ATCTTAATTA      1080

TATACTTTTG  ATTACCCTCA  AAAACCATCC  ACTAAAGCCA  AACATATTAT  AGTATTAACT      1140

ATTAATATTA  AGGATAAAAC  TACAACTCAA  AACCAACTAA  GCTT                        1184
```

( 2 ) INFORMATION FOR SEQ ID NO:5:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: other nucleic acid ( i v ) ANTI-SENSE: NO ( x i ) SEQUENCE DESCRIPTION: SEQ ID NO:5:

```
AGCGGCCGCT                                                                    10
```